United States Patent
Henriksson et al.

(10) Patent No.: US 8,758,517 B2
(45) Date of Patent: *Jun. 24, 2014

(54) PROCESS FOR THE HYDROLYSIS OF CELLULOSE

(75) Inventors: Gunnar Henriksson, Solna (SE); Mikael Lindstrom, Lidingo (SE)

(73) Assignee: Re:Newcell Lux S.a.r.l, Luxembourg (LU)

(*) Notice: Subject to any disclaimer, the term of this patent is extended or adjusted under 35 U.S.C. 154(b) by 126 days.

This patent is subject to a terminal disclaimer.

(21) Appl. No.: 13/265,353

(22) PCT Filed: Apr. 16, 2010

(86) PCT No.: PCT/EP2010/055030
§ 371 (c)(1),
(2), (4) Date: Oct. 20, 2011

(87) PCT Pub. No.: WO2010/124944
PCT Pub. Date: Nov. 4, 2010

(65) Prior Publication Data
US 2012/0040411 A1 Feb. 16, 2012

Related U.S. Application Data

(60) Provisional application No. 61/173,548, filed on Apr. 28, 2009.

(30) Foreign Application Priority Data

Apr. 29, 2009 (SE) .................................. 0950287

(51) Int. Cl.
C13K 1/02 (2006.01)
C13K 1/04 (2006.01)
C08B 1/08 (2006.01)
A61K 38/00 (2006.01)

(52) U.S. Cl.
USPC ............. 127/37; 435/209; 435/163; 435/165; 8/518

(58) Field of Classification Search
CPC ............................. C12P 2203/00; C08B 15/08
See application file for complete search history.

(56) References Cited

U.S. PATENT DOCUMENTS

| | | | |
|---|---|---|---|
| 3,990,945 A | 11/1976 | Huff et al. | |
| 4,033,910 A * | 7/1977 | Papa | 521/131 |
| 4,089,745 A | 5/1978 | Antrim et al. | |
| 4,174,976 A | 11/1979 | Tsao et al. | |
| 4,752,579 A | 6/1988 | Arena et al. | |
| 5,620,877 A | 4/1997 | Farone et al. | |
| 6,045,683 A * | 4/2000 | Riley et al. | 205/318 |
| 2004/0231661 A1* | 11/2004 | Griffin et al. | 127/1 |
| 2005/0192434 A1* | 9/2005 | Buchanan et al. | 536/32 |
| 2008/0102502 A1 | 5/2008 | Foody et al. | |
| 2010/0285295 A1* | 11/2010 | Wang et al. | 428/292.4 |
| 2011/0091940 A1* | 4/2011 | Atalla | 435/105 |

FOREIGN PATENT DOCUMENTS

| | | |
|---|---|---|
| EP | 0 344 371 A1 | 12/1989 |
| WO | 96/40970 | 12/1996 |
| WO | 2008/086115 A2 | 7/2008 |
| WO | 2008/095098 A2 | 8/2008 |

OTHER PUBLICATIONS

Filson et al. (2009) Available on line Dec. 23, 2008 "Sono-chemical preparation of cellulose nanocrystals from lignocellulose derived materials", Bioresource Technol., vol. 100, pp. 2259-2264.*
Sun et al. (20020 Hydrolysis of lignocellulosic materials for ethanol production: a review, Bioresource Technol., vol. 83, pp. 1-11.*
Sun et al. (2002) Hydrolysis of lignocellulosic materials for ethanol production: a review, Bioresource Technol., vol. 83, pp. 1-11.*
Filson et al. (2009) "Sono-chemical preparation of cellulose nanocrystals from lignocellulose derived materials", Bioresource Technol., vol. 100, pp. 2259-2264.*
Zhao et al., Enhanced Enzymatic Hydrolysis of Spruce by Alkaline Pretreatment at Low Temperature, Biotechnology and Bioengineering, vol. 99, No. 6, 2008, pp. 1320-1328.
Jeihanipour et al., Ethanol production from cotton-based waste textiles, Bioresource Technology, vol. 100, 2009, pp. 1007-1010.
International Search Report for corresponding International Application No. PCT/EP2010/055030 mailed Sep. 23, 2010.
Written Opinion of the International Searching Authority for corresponding International Application No. PCT/EP2010/055030 mailed Sep. 23, 2010.
Notification of Transmittal of the International Preliminary Report on Patentability for corresponding International Application No. PCT/EP2010/055030 mailed Apr. 8, 2011.

* cited by examiner

Primary Examiner — Karen Cochrane Carlson
Assistant Examiner — Samuel Liu
(74) Attorney, Agent, or Firm — Renner, Otto, Boisselle & Sklar, LLP

(57) ABSTRACT

There is disclosed a process for the hydrolysis of cellulose comprising the sequential steps (a) mixing cellulose with a viscosity below 900 ml/g with an aqueous solution to obtain a liquid, wherein particles comprising cellulose in said liquid have a diameter of maximum 200 nm, wherein the temperature of the aqueous solution is below 35° C., and wherein the pH of the aqueous solution is above 12, (b) subjecting the liquid to at least one of the steps: (i) decreasing the pH of the liquid with at least 1 pH unit and (ii) increasing the temperature by at least 20° C., and (c) hydrolyzing the cellulose. Moreover there is disclose glucose manufactured according to the method and ethanol manufactured from the glucose. Advantages include that the cellulose is hydrolyzed faster and to a greater extent after the treatment. The yield is increased.

20 Claims, No Drawings

PROCESS FOR THE HYDROLYSIS OF CELLULOSE

This application is a national phase of International Application No. PCT/EP2010/055030 filed Apr. 16, 2010 and published in the English language, which claims priority to U.S. 61/173,548 filed Apr. 28, 2009 and SE 0950287-3 filed Apr. 29, 2009.

TECHNICAL FIELD

The present invention relates to a process for improving the degradation of cellulose.

BACKGROUND

Cellulose is an important constituent in plants and comprises anhydrous glucose units. When cellulose is depolymerised glucose may be obtained, which can be used for many different purposes including manufacture of ethanol using yeast.

The degradation of cellulose is complicated due to the resistibility of the material.

When cellulose is hydrolyzed with strong acid, by-products are formed which may act as inhibitors for the yeast in a subsequent step in the manufacture of ethanol. In order to achieve a total degradation of cellulose a long duration of the hydrolysis is required and during a prolonged hydrolysis dissolved cellulose may react further and form inhibitors for yeast.

Another approach is to degrade cellulose with enzymes. However the present enzymatic processes are expensive mainly because they are slow and that the enzymes are relatively expensive.

Yet another approach is hydrolysis with diluted acid. This approach also suffers from problems with slow degradation.

There are several known ways to dissolve cellulose for various applications including manufacture regenerated cellulosic fiber. Often expensive chemicals are used in such processes.

Zhao et al, in Biotechnology and Bioengineering, pp. 1320-1328, Vol. 99, No. 6, 2008 discloses treatment of wood fiber bundles with NaOH and NaOH/Urea. There is disclosed treatment with cold NaOH. The treated pulp is neutralized. Any cellulose which is dissolved in the NaOH solution is apparently not used further. It is disclosed that treatment with cold NaOH is advantageous. The yield is improved with pretreatment.

WO 2008/095098 discloses a process for the manufacture of sugar from biomass, where the biomass is pretreated with alkali solution to improve the following hydrolysis. The temperature is increased and is 50-150° C., preferably 80-140° C.

Jeihanipour et al, in Biorecource Technology, pp. 1007-1010, Vol. 100, 2009 discloses alkali pretreatment of cotton linter followed by enzymatic hydrolysis. It is disclosed that low temperatures improves the process. The cellulose material which is used is not dissolved or suspended in the alkali solution, it remains solid. A problem in this technology is that some of the cellulose material dissolves and is discarded, which reduces the yield.

EP 0 344 371 A1 discloses a method for the production of monosaccharides by hydrolysis of lignocellulosic materials. There is no dissolution of the cellulose, where the dissolved cellulose is recovered. The cellulose is washed, but cellulose that is dissolved is apparently not recovered.

U.S. Pat. No. 4,089,745 discloses a process for enzymatic conversion of corn hull cellulose to glucose. Again there is no dissolution of the cellulose, where the dissolved cellulose is recovered. The cellulose is washed, but cellulose that is dissolved is apparently not recovered.

US 2008/0102502 A1 concerns recovery of inorganic salt during processing of lignocellulosic feedstocks. It is mentioned that carbon dioxide can be used to adjust pH.

There is a need for an improved process for the degradation of cellulose.

SUMMARY

It is an object of the present invention to obviate at least some of the disadvantages in the prior art and to provide an improved process for the treatment of cellulose.

In a first aspect there is provided a process for the hydrolysis of cellulose comprising the sequential steps: (a) mixing cellulose with a viscosity below 900 ml/g with an aqueous solution to obtain a liquid, wherein particles comprising cellulose in said liquid have a diameter of maximum 200 nm, wherein the temperature of the aqueous solution is below 35° C., and wherein the pH of the aqueous solution is above 12, (b) subjecting the liquid to at least one of the steps: (i) decreasing the pH of the liquid with at least 1 pH unit and (ii) increasing the temperature by at least 20° C., and (c) hydrolyzing the cellulose.

In a second aspect there is provided glucose manufactured according to the process.

In a third aspect there is provided ethanol manufactured according to the process.

Further aspects and embodiments are defined in the appended claims, which are specifically incorporated herein by reference.

Advantages include that there is provided the possibility to hydrolyze cellulose faster and to a greater extent after the treatment with an improved yield.

One advantage is that the yield is increased compared to methods which discard an alkali treatment solution. In the present method the cellulose material is treated with an alkali solution, and the alkali solution, which inevitably comprises cellulose is not discarded.

Another advantage is that the liquid is possible to pump since it is a solution and/or a colloidal system with particles not larger than 200 nm.

Another advantage is that the waste of cellulose material is reduced or even eliminated.

Yet another advantage is that the hydrolyzed cellulose is easier to ferment to for instance ethanol, since less or no by-products are formed during the hydrolysis.

Another advantage is that the process can be used both for enzymatic and acid hydrolysis of cellulose.

Compared to known methods the present process is easy to perform in a large scale set up.

DEFINITIONS

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

Unless clearly indicated, all percentages are calculated by weight.

The term "about" as used in connection with a numerical value throughout the description and the claims denotes an interval of accuracy, familiar and acceptable to a person skilled in the art. Said interval is ±10%.

"Colloid system" is used herein to denote a system comprising two separate phases, a dispersed phase and a continuous phase. The dispersed phase comprises particles with an average diameter of between 5-200 nm. In the present invention a colloidal system comprises particles comprising cellulose with an average diameter of between 5-200 nm in a continuous aqueous phase, where the aqueous phase may comprise dissolved cellulose and other dissolved substances.

"Diameter" of an irregular particle as used herein is the longest distance between two points on its surface.

"Fluid" is used herein to denote a substance that continually deforms (flows) under an applied shear stress. Fluid comprises all liquids and all gases.

"Hydrolysis" is used herein to denote a process in which a chemical compound is decomposed by interaction with water.

"Liquid" is used herein to denote a fluid that can freely form a distinct surface at the boundaries of its bulk material. The term liquid encompasses both solutions as well as colloidal systems such as a colloidal suspension.

"Solution" is used herein to denote a homogeneous mixture comprising at least one substance dissolved in a solvent.

The term "viscosity" for an aqueous cellulose mixture is a standard term within in pulp and paper industry. The term is well known by persons skilled in the art of cellulose including pulp and paper making. Its value is related to the average degree of polymerization of the cellulose, i.e. how long the individual cellulose chains are. A high value indicates that the cellulose has long chains and high degree of polymerization, whereas a low value indicates that the cellulose have low degree of polymerization. The viscosity value is proportional to the average molecular weight of the cellulose molecules. The limiting viscosity number ("viscosity") in the present description and in the appended claims is determined according to ISO 5351. "Pulps—Determination of limiting viscosity number in cupri-ethylenediamine (CED) solution Reference number 5351:2004(E), International Organization for Standardization, Geneva, Switzerland.

DETAILED DESCRIPTION

There is provided a process for the hydrolysis of cellulose comprising the sequential steps: (a) mixing cellulose with a viscosity below 900 ml/g with an aqueous solution to obtain a liquid, wherein particles comprising cellulose in said liquid have a diameter of maximum 200 nm, wherein the temperature of the aqueous solution is below 35° C., and wherein the pH of the aqueous solution is above 12, (b) subjecting the liquid to at least one of the steps: (i) decreasing the pH of the liquid with at least 1 pH unit and (ii) increasing the temperature by at least 20° C., and (c) hydrolyzing the cellulose.

The cellulose is mixed with the aqueous solution so that a liquid is obtained. The liquid which is obtained is either a solution of cellulose in the aqueous solution or a combination of a solution of cellulose and a colloidal system with dispersed particles comprising cellulose in the aqueous solution.

The particles comprising cellulose have a diameter of 200 nm or less. In one embodiment the particle diameter is from about 5 nm to about 200 nm.

In one embodiment the viscosity of the cellulose is below 900 ml/g. In one embodiment the viscosity of the cellulose is below 700 ml/g.

In one embodiment there is a step before step a), wherein the viscosity of cellulose with a viscosity above 900 ml/g is lowered to below 900, preferably below 700 ml/g. This is particularly useful when cellulose with a viscosity above 900 ml/g is to be treated. In one embodiment treatment with acid is used to reduce the viscosity of the cellulose.

In alternative embodiments the degradation is performed using a radical generating system. Examples include the Fenton reaction, (i.e. transition metal ions and hydrogen peroxide), hypochlorite, and alkaline hydrolysis at high temperature. More precise Fenton's reagent is a solution of hydro hydrogen peroxide and an iron catalyst. In one embodiment the viscosity is lowered before step a) by treatment with at least one method selected from treatment with Fenton's reagent and treatment with an alkaline solution.

In one embodiment the aqueous solution in step a) comprises at least one strong base. In one embodiment the aqueous solution in step a) comprises NaOH. NaOH is a suitable and economical way of achieving a high pH in this method. In one embodiment the aqueous solution comprises at least 2 wt % NaOH. In one embodiment the aqueous solution comprises at least 5 wt % NaOH. In one embodiment the aqueous solution comprises at least 8 wt % NaOH. In one embodiment the aqueous solution comprises at least 10 wt % NaOH.

In one embodiment the liquid is filtered between step a) and step b). In another embodiment the liquid if centrifuged between step a) and step b) in order to remove impurities. It is an advantage that the process provides this possibility to remove impurities which have not dissolved in the liquid.

In one embodiment the pH is decreased in step b) by addition of an acid. This has the effect of precipitating the cellulose from the liquid. In one embodiment the acid is sulphuric acid.

In an alternative embodiment the pH is decreased in step b) by addition of $CO_2$. Also $H_2CO_3$ may be employed particularly in combination with $CO_2$. Thus there is disclosed an embodiment where the pH is decreased in step b) by addition of at least one chemical entity selected from $CO_2$, and $H_2CO_3$. This is advantageous for use in an industrial scale, where $CO_2$ can be recycled in the process according to methods well known to a person skilled in the art of papermaking.

In one embodiment the temperature is below 20° C. in step a). In one embodiment the temperature is below 15° C. in step a). In one embodiment the temperature is below 10° C. in step a). In one embodiment the temperature is below 4° C. in step a). A lower temperature is beneficial although the process can be carried out at room temperature, i.e. at about 20° C.

In one embodiment cellulose which has not been dissolved and/or suspended to a particle size below 200 nm in step a) is recycled to step a). In this way any waste of cellulose can be minimized. In one embodiment fibers which are larger than 200 nm are removed in step a).

In one embodiment step b) is followed by an enzymatic hydrolysis of the cellulose. The cellulose is hydrolyzed to produce glucose.

In an alternative embodiment step b) is followed by acid hydrolysis of the cellulose.

In one embodiment the product from the hydrolysis is used for the manufacture of ethanol. The glucose formed during the hydrolysis is used for the manufacture of ethanol. In one embodiment the ethanol is manufactured by fermentation. Fermentation of glucose to ethanol is well known and familiar to a person skilled in the art.

In a second aspect there is provided glucose manufactured by hydrolysis according to the above process. The glucose can be used in many ways including the manufacture of ethanol, and as starting material for different polymers/chemicals.

In a third aspect there is provided ethanol manufactured according to the above process. The ethanol can for instance be used as a fuel additive for automotive fuels.

Other features and uses of the invention and their associated advantages will be evident to a person skilled in the art upon reading this description and the appended examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Dissolution of Different Celluloses at 4° C.

Cellulose quality: Avicel (Microcrystalline cellulose), cotton linter, sulphite pulp, birch kraft pulp. Viscosity of the samples were measured according to ISO 5351. This is a method to get a viscosity value that is dependent on the degree of polymerization of mainly the cellulose in the samples; the higher the viscosity, the higher the average degree of polymerization of the samples.

Treatment conditions: Every 1 g sample was added to 50 ml 10% NaOH at 4° C., and subjected to magnetic stirring for approx 1 h.

The solutions were evaluated for how clear they appeared.

| sample | appearance | Viscosity (ml/g) |
|---|---|---|
| Avicel | One phase and transparent | 120 |
| Birch kraft pulp | Some suspended substance in the solution, not totally dissolved | 710 |
| Cotton linter | Some suspended substance in the solution, not totally dissolved | 900 |
| Sulphite pulp | Some suspended substance in the solution, not totally dissolved | 550 |

Only Avicel is totally dissolved. The other one are not totally in one phase. The Avicel has shorter cellulose chains. The non transparent samples indicate that the cellulose has not dissolved completely.

Example 2

Dissolution in Varying Concentration of Cellulose

Cellulose quality: Avicel (Microcrystalline cellulose)

Treatment conditions: 1 g or 2 g cellulose were added to 50 ml 10% NaOH at varying temperature, and subjected to magnetic stirring for approx 1 h.

| | appearance | |
|---|---|---|
| Temperature | 1 g sample | 2 g sample |
| 4° C. | One phase and transparent | One phase, not so transparent, a little bit milky |
| 10° C. | One phase and transparent | One phase, milky |
| Room Temperature | One phase, not so transparent | One phase, light yellow color |
| 40° C. | Two phases, some precipitate | — |

Example 3

Dissolution at Varying Concentration

Cellulose quality: Avicel (Microcrystalline cellulose)

Treatment conditions: Samples 0.05 g, 0.1 g, 0.25 g, 0.5 g, 1 g Avicel in 50 ml 1%, 5%, 8%, 10% NaOH respectively. All experiments were done at 4° C.

The solutions were evaluated for if the Avicel dissolved.

| | $C_{NaOH}$ | | | |
|---|---|---|---|---|
| Avicel/g | 1% | 5% | 8% | 10% |
| 0.1 | dissolved | dissolved | dissolved | dissolved |
| 0.2 | dissolved | dissolved | dissolved | dissolved |
| 0.5 | Not dissolved | dissolved | dissolved | dissolved |
| 1 | — | — | — | dissolved |
| 2 | — | — | — | dissolved |

Along with the increase of the concentration of NaOH, more Avicel will be dissolved (as a reference a solution of 2% NaOH has a pH of about 12.8 at 25° C.).

Example 4

Acidic Hydrolysis in 40% Sulphuric Acid Varying Pretreatment Temperature

Cellulose quality: Avicel (Microcrystalline cellulose) and Avicel pretreated with NaOH.

Treatment conditions: acidic hydrolysis of the 1 g, 2 g samples with 40% sulphuric acid in 90° C. water bath for 1 h and 3 h respectively.

The evaluation was done by measuring the weight of the residue solid.

| Name of sample | Time | Weight of residue solid | |
|---|---|---|---|
| | | 1 g sample/g | 2 g sample/g |
| Original Avicel | 1 h | 0.357 | 0.944 |
| | 3 h | 0.336 | 0.896 |
| Pre-treated in 4° C. | 1 h | 0.032 | 0.45 |
| | 3 h | 0.008 | 0.179 |
| Pre-treated in 10° C. | 1 h | 0.035 | 0.35 |
| | 3 h | 0.007 | 0.28 |
| Pre-treated in RT | 1 h | 0.041 | 0.492 |
| | 3 h | 0.015 | 0.284 |

For the 1 g samples the pretreatment at higher temperatures give a strong effect for the degradation. Also for the 2 g sample there was pronounced effect.

Example 4

Enzymatic Hydrolysis of Pretreated Samples Varying Pretreatment Temperature

Cellulose quality: Avicel (Microcrystalline cellulose) and pretreated Avicel with NaOH.

The pretreatment was done by dissolving the Avicel 1 g) in 50 ml 10% NaOH at 4° C. Precipitation was done by adjusting the pH to 7 with sulphuric acid.

Treatment conditions: Enzymatic hydrolysis of the 1 g, or 2 g samples with 1 ml NOVOZYM 342® enzyme (A semi commercial product from Novozymes NS comprising cellulases) and 30 ml 20 mM sodium phosphate buffer (pH=7.01) in 40° C. water bath for 5 h and 20 h.

The evaluation was done by measuring the weight of the residue solid. Compensation for water content was done ("Dry weight").

| Name of samples | Time | Weight of residue solid | |
|---|---|---|---|
| | | 1 g sample/g | 2 g sample/g |
| Original Avicel | 5 h | 0.862 | 1.797 |
| | 20 h | 0.835 | 1.682 |
| Pre-treated in 4° C. | 5 h | 0.47 | 1.217 |
| | 20 h | 0.248 | 0.621 |
| Pre-treated in 10° C. | 5 h | 0.44 | 1.269 |
| | 20 h | 0.185 | 0.799 |
| Pre-treated in RT | 5 h | 0.594 | 1.265 |
| | 20 h | 0.303 | 1.101 |

It is clear that the pretreatment gives an improved degradation for both the 1 g and the 2 g samples. A lower temperature gives an improved result, at least for the 2 g samples.

Example 5

Dissolution at Varying Concentration

Cellulose quality: Avicel (Microcrystalline cellulose)

Treatment conditions: 0.05 g, 0.25 g, 0.5 g, 1 g, 2.5 g, 5 g cellulose were added to 50 ml 10% NaOH at 4° C., and subjected to magnetic stirring for approx 1 h.

The solutions were evaluated for how clear they were.

| Avicel/g | appearance |
|---|---|
| 0.1 | Very clear solution |
| 0.5 | One phase and transparent, but not very clear |
| 1.0 | One phase, transparent |
| 2 | One phase, transparent |
| 4 | One phase, not transparent, a little bit light yellow color |
| 5 | Nearly opacity, like a colloid |
| 10 | Cannot be dissolved |

When the Avicel concentration reached a certain point, the sample will become a colloid, and not a true solution. During the dissolving stage, stirring is very important, strong stirring can dissolve the Avicel easily and fast.

Example 6

Dissolution at Varying Temperature

Cellulose quality: Avicel (Microcrystalline cellulose)

Treatment conditions: 1 g cellulose were added to 50 ml 10% NaOH at varying temperature, and subjected to magnetic stirring for approx 1 h. The effect was mostly done within 10 minutes.

The solutions were evaluated for how clear they were. Photos were taken in some cases.

| Temperature | appearance |
|---|---|
| 4° C. | One phase and transparent |
| 10° C. | One phase and transparent |
| Room Temperature | One phase, not so transparent |
| 40° C. | Two phases, some precipitate |

All of the celluloses were dissolved in 4° C., 10° C. and room temperature, but at 40° C. when the magnetic stir is stopped, some precipitate occurred. At room temperature a stable suspension is obtained, which can be treated as a fluid from a technical point of view.

Example 7

Acidic Hydrolysis Varying Concentration of Sulphuric Acid

Cellulose quality: Avicel (Microcrystalline cellulose) and pretreated Avicel with NaOH.

Treatment conditions: Acidic hydrolysis of the 1 g samples with 0.1M or 40% sulphuric acid in 90° C. water bath for 20 min, 40 min, 1 h, 2 h, 5 h. This experiment was done with untreated Avicel and Avicel that had been dissolved in 50 ml 10% NaOH at 4° C. Precipitation was done by adjusting the pH to 7 with sulphuric acid.

The evaluation was done by measuring the weight of the residue solid.

Acidic hydrolysis with 0.1M $H_2SO_4$

| time/h | Avicel/g | pre-treated sample/g |
|---|---|---|
| 1/6 | 0.952 | 0.924 |
| 1/3 | 0.953 | 0.918 |
| 2/3 | 0.948 | 0.906 |
| 1 | 0.946 | 0.913 |
| 2 | 0.943 | 0.897 |
| 5 | 0.942 | 0.901 |

Acidic hydrolysis with 40% $H_2SO_4$

| time/h | Avicel/g | pretreated sample/g |
|---|---|---|
| 1/6 | 0.674 | 0.444 |
| 1/3 | 0.684 | 0.511 |
| 2/3 | 0.624 | 0.434 |
| 1 | 0.559 | 0.492 |
| 2 | 0.391 | 0.142 |
| 5 | 0.358 | 0.044 |

The effects are large for the hydrolysis with 40% $H_2SO_4$ It is faster and the non pretreated cellulose tends to reach only 60% degradation. The very dilute acid did not achieve strong degradation for any of the celluloses, but nevertheless there was a significant difference between the pretreated cellulose and the control.

Example 8

Enzymatic Hydrolysis of Pretreated Cellulose Varying Time

Cellulose quality: Avicel (Microcrystalline cellulose) and pretreated Avicel with NaOH. The pretreatment was done by dissolving 1 g Avicel in 50 ml 10% NaOH solution at 4° C. and then precipitated the sample with sulphuric acid, i.e., adjusting the pH to pH 7 at room temperature.

Treatment conditions: 1 g treated cellulose was mixed with 1 ml NOVOZYM 342® enzyme (corresponding to 90 ECU. ECU is an enzyme activity unit used by the manufacturer and described in the publication "Determination of Endo-Cellulase Activity using CMC Vibration Viscometry" published by Novozymes A/S.) and 30 ml 20 mM sodium phosphate buffer (pH=6.96) in 40° C. water bath for 30 min, 2 h, 4 h, 7 h, 24 h, 48 h. NOVOZYM 342® enzyme is a commercial mixture of cellulose degrading enzymes produced by the company Novozymes A/S.

The evaluation was done by measuring the weight of the residue solid, i.e. the cellulose that was not degraded

| Time/h | Untreated Avicel/g | Pretreated sample/g |
|---|---|---|
| 0.5 | 0.94 | 0.708 |
| 2 | 0.919 | 0.622 |
| 4 | 0.885 | 0.54 |
| 7 | 0.884 | 0.391 |
| 24 | 0.746 | 0.221 |
| 48 | 0.622 | 0.137 |

As shown in the table the degradation is much faster for the pretreated cellulose. In principal this can be utilized in two different ways; either to increase the yield of the degradation—as seen after 40 h incubation around 85% of the cellulose is degraded in the pretreated cellulose, whereas only 35% is degraded of the untreated control, or to perform a degradation to a specific yield and thereby do the degradation much faster; as shown in the figure 50% degradation of the pretreated cellulose can be obtained after around 5 h, whereas for the untreated control this takes maybe 60 h (it is outside the incubation time).

Example 8

Precipitation of Cellulose with Carbon Dioxide

Cellulose quality: Avicel (Microcrystalline cellulose)
Treatment conditions: 1 g Avicel was dissolved in 50 ml 10% NaOH solution at 4° C., and then either precipitate it with sulphuric acid (pH adjusted to pH 7) or by flushing carbon dioxide gas. A beaker with the solution was flushed with carbon dioxide gas meanwhile the solution was stilled by magnetic stirring. The precipitate come quick, but the flushing was continued for 1 h. The pH was then 10. A continuous 30 min of flushing did not change the pH.

The precipitates were collected and weight.

The yield of the carbon dioxide precipitation was 86.1%, and the acid precipitation was close to 100%

The results show that adjustment of pH with carbon dioxide (that forms carbonic acid) can be used for precipitating cellulose, although the yield was lower than in the case of pH adjustment with sulphuric acid. The results also show that the precipitate comes at higher pH than 7.

It has several advantages to perform cellulose precipitation with carbon dioxide, since this make closing of process streams in a pulp mill, easier. This since the sodium carbonate formed during the precipitation can be reconverted to sodium hydroxide with a lime cycle. In this process carbon dioxide is formed that can be used for the precipitation.

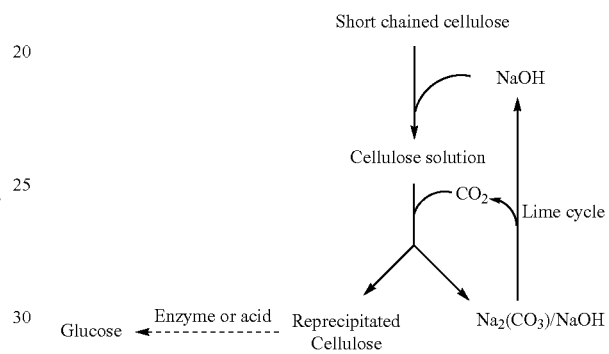

Example 9

Acidic and Enzymatic Hydrolysis of 40° C. Pretreated Samples

Cellulose quality: Avicel (Microcrystalline cellulose) pretreated with NaOH, the pretreatment was done by "dissolving" 1 g Avicel in 50 ml 10% NaOH at 40° C., or lower temperature and then neutralized by sulphuric acid to pH7 at room temperature.

Treatment conditions: Acidic hydrolysis with 40% sulphuric acid in 90° C. water bath for 1 h and 3 h. Do enzymatic hydrolysis of the 1 g samples with 1 ml NOVOZYM 342® enzyme and 30 ml 20 mM sodium phosphate buffer (pH=7.01) in 40° C. water bath for 5 h and 20 h.

Evaluation The evaluation was done by measuring the weight of the residue solid.

Acidic hydrolysis of 40° C. pretreated samples with 40% sulphuric acid:

| sample | residue solid/g |
|---|---|
| 1 g(1 h) | 0.431 |
| 1 g(3 h) | 0.363 |
| 2 g(1 h) | 0.956 |
| 2 g(3 h) | 0.81 |

Enzymatic hydrolysis with NOVOZYM 342® enzyme:

| sample | original Avicel/g | pre-treated 40° C./g | pre-treated 20° C.(RT)/g | pre-treated 10° C./g | pre-treated 4° C./g |
|---|---|---|---|---|---|
| 1 g(5 h) | 0.862 | 0.686 | 0.594 | 0.44 | 0.47 |
| 1 g(20 h) | 0.835 | 0.548 | 0.303 | 0.185 | 0.248 |
| 2 g(5 h) | 1.797 | 1.593 | 1.265 | 1.269 | 1.217 |
| 2 g(20 h) | 1.682 | 1.324 | 1.101 | 0.799 | 0.621 |

The result on the enzymatic degradation shows that the effect is clearly better if the dissolution is done at lower temperature. At 40° C. no real dissolution happens, but there is still an improvement, at least by the enzymatic degradation.

Example 10

Enzymatic Hydrolysis of Alkaline Pretreated Cellulose of Varying Qualities

Cellulose Qualities:
Avicel (Microcrystalline cellulose), Viscosity 120 ml/g. This cellulose has a low degree of polymerization but has a very high degree of crystallinity. Crystallinity index 0.88.

Fully bleached mixed spruce and pine sulphite pulp, Viscosity 550 ml/g. This cellulose has a relative low degree of polymerization. It is pulped at acidic condition and has a rather high crystallinity. Crystallinity index 0.53.

Fully bleached birch kraft pulp, Viscosity 710 ml/g. This cellulose has a rather high degree of polymerization. It is pulped during alkaline condition and contains most likely a portion of unordered swelled cellulose. Crystallinity index 0.43.

Cotton linters, Viscosity 900 ml/g. This cellulose is not pulped and has a very high degree of polymerization. Most of the celluloses have a high degree of crystallinity. Crystallinity index 0.66.

Treatment conditions: All cellulose qualities were pretreated with NaOH solution. The pretreatment was done by dissolving 1 g dry weight cellulose in 50 ml 10% NaOH solution at 4° C. and then precipitated the sample with sulphuric acid (neutralize the solution to pH 7).

The samples were subjected to enzymatic hydrolysis of the 1 g samples with 1 ml NOVOZYM 342® enzyme and 30 ml 20 mM sodium phosphate buffer (pH=6.97) in 40° C. water bath for 5 h and 20 h.

Evaluation The evaluation was done by measuring the weight of the residue solid.

Untreated sample after hydrolysis

| time | Avicel/g | sulphite pulp/g | birch kraft pulp/g | cotton linter/g |
|---|---|---|---|---|
| 5 h | 0.862 | 0.906 | 0.703 | 0.888 |
| 20 h | 0.835 | 0.783 | 0.535 | 0.79 |

Pre-treated sample:

| time | Avicel/g | sulphite pulp/g | birch kraft pulp/g | cotton linter/g |
|---|---|---|---|---|
| 5 h | 0.47 | 0.61 | 0.433 | 0.71 |
| 20 h | 0.248 | 0.439 | 0.327 | 0.584 |

The results indicate that of the untreated samples, the kraft pulp is the easiest to degrade, with Avicel as the most difficult. This indicates that the degree of crystallinity is important for the degradation rate. The pretreatment worked differently well for the different cellulose qualities; the largest improving effects are on Avicel, followed by sulphite pulp, and the smallest effects were on cotton linters. This indicates that low degree of polymerization is important for the efficiency of the technique to increase the cellulose reactivity works better on shorted chained cellulose than on longer. Furthermore, the relative reactivity increase is more pronounced for cellulose with higher crystallinity.

The stimulating effect was present for all samples, demonstrating that the method is robust. From this data it is clear that a shortening of the cellulose in long chained material with for instance acid hydrolysis will increase the effectiveness of the method.

Example 11

Dissolution at Varying Concentration"

Cellulose quality: Avicel (Microcrystalline cellulose)
Treatment conditions: Samples 0.05 g, 0.1 g, 0.25 g, 0.5 g, 1 g Avicel in 50 ml 1%, 5%, 8%, 10% NaOH respectively. All experiments were done at 4° C.

The solutions were evaluated for if the Avicel dissolved.

| | $C_{NaOH}$ | | | |
|---|---|---|---|---|
| Avicel/g | 1% | 5% | 8% | 10% |
| 0.1 | dissolved | dissolved | dissolved | dissolved |
| 0.2 | dissolved | dissolved | dissolved | dissolved |
| 0.5 | Not dissolved | dissolved | dissolved | dissolved |
| 1.0 | Not dissolved | Not dissolved | dissolved | dissolved |
| 2 | — | — | dissolved | dissolved |
| 4 | — | — | dissolved | dissolved |
| 10 | — | — | — | Gel like. |

Along with the increasing of the concentration of NaOH, more Avicel will be dissolved.

It is possible to perform dissolution of short chain cellulose to at least 4% in 8% and 10% NaOH respectively. 10% is too high a cellulose concentration. Lower concentrations of alkali can dissolve low concentrations of cellulose.

Example 12

The Role of Cellulose Concentration During the Dissolution in Alkali

Cellulose quality: Avicel (Microcrystalline cellulose)
Treatment conditions: The cellulose was pretreated with NaOH, by dissolving 1 g Avicel in different volume of 10% NaOH, so that the cellulose concentration in the solutions varied between 0.5% and 5%, at room temperature and then neutralized with sulphuric acid to pH 7. The cellulose was precipitated and collected with approx 100% yield. The samples (never dried) were hydrolyzed with 11-12 ml 40% sulphuric acid in 90° C. water bath for 2 h.

The evaluation was done by measuring the weight of the solid residue after hydrolysis. Note the solid residue was determined with filtrations instead of centrifugation in the experiment.

| sample | residue solid/g | volume of NaOH/ml |
|---|---|---|
| 5% | 0.358 | 20 |
| 3% | 0.307 | 33.3 |
| 2% | 0.263 | 50 |
| 1% | 0.167 | 100 |
| 0.50% | 0.14 | 200 |

Untreated Avicel is degraded to 0.556.

This experiment shows that the effects of the dissolution and precipitation of cellulose on the degradability is enhanced by high volumes of alkali solution, i.e., low cellulose concentrations.

Example 13

Precipitation with Varying Temperature or pH

Cellulose quality: Avicel (Microcrystalline cellulose) pretreated with NaOH, the pretreatment was done by dissolving 1 g Avicel in 50 ml 10% NaOH at 4° C.

Treatment conditions: Attempts to precipitate the solution were performed according to two different strategies; Neutralizing the solution with sulphuric acid to pH approx 7, 9, and 11 (pH was determined) at 4° C., or increasing the temperature which is done by putting the solution into 100° C. water bath for 1.5 hours.

The evaluation was done by measuring the yield of the precipitation. A filtration method was used. The pH before precipitation was 14-14.6

| Precipitation method | Weight of the precipitation/g | yield |
|---|---|---|
| Neutralize to pH 7.04 | 1.008 | 100.0% |
| Neutralize to pH 9.04 | 0.990 | 99.0% |
| Neutralize to pH 11.30 | 1.009 | 100.0% |
| Only increasing the temperature to >90° C. | 0.355 | 35.5%. The precipitate became yellow. |

In the previous examples the precipitation was performed by a combined increase of the temperature and decrease of pH to approximately neutral. Here the effects of lowering the pH lowering and increasing the temperature were investigated separately. The results show clearly that the most of the effect is achieved by lowering the pH. This implies that it is possible to run the process at constant temperature, which is advantageous since the sample does not have to undergo energy consuming temperature changes. The pH lowering can also be much smaller than what we have used earlier; a decrease to a pH around 11 seems to be enough, which is beneficial from an economical point of view. To use the same pH and only increase the temperature is an option, but seems to be less preferred for most applications. The yield of the precipitation at an increase of temperature to close to 100° C. was only around 35%, and the formation of yellow color indicates that the cellulose has undergone structural changes. Something that is likely under this very high temperature and alkalinity.

The invention claimed is:

1. A process for the hydrolysis of cellulose comprising the sequential steps:
    a) mixing cellulose with having a viscosity below 900 ml/g with an aqueous solution free of cosolvents to obtain a liquid, wherein particles comprising cellulose which are resulted from said liquid have a diameter of maximum 200 nm, wherein the temperature of the aqueous solution is below 20° C., and wherein the pH of the aqueous solution is above 12,
    b) subjecting the liquid to at least one of the steps:
        i) decreasing the pH of the liquid with at least 1 pH unit, and
        ii) increasing the temperature by at least 20° C., and
    c) hydrolyzing the cellulose.

2. The process according to claim 1, wherein the viscosity of the cellulose is below 700 ml/g.

3. The process according to claim 1, further comprising a step before step a), wherein the viscosity of the cellulose is lowered to below 900 ml/g.

4. The process according to claim 3, wherein the viscosity is lowered by treatment with acid.

5. The process according to claim 3, wherein the viscosity is lowered by treatment with at least one selected from the group consisting of Fenton reagent and an alkaline solution.

6. The process according to claim 1, wherein the aqueous solution comprises NaOH.

7. The process according to claim 1, wherein the aqueous solution comprises at least 2 wt % NaOH.

8. The process according to claim 1, wherein the liquid is filtered between step a) and step b).

9. The process according to claim 1, wherein the liquid is centrifuged between step a) and step b).

10. The process according to claim 1, wherein the pH is decreased in step b) by addition of an acid.

11. The process according to claim 10, wherein the acid is sulphuric acid.

12. The process according to claim 1, wherein the pH is decreased in step b) by addition of at least one chemical entity selected from $CO_2$, and $H_2CO_3$.

13. The process according to claim 1, wherein the temperature is below 15° C. in step a).

14. The process according to claim 1, wherein the temperature is below 10° C. in step a).

15. The process according to claim 1, wherein the temperature is below 4° C. in step a).

16. The process according to claim 1, wherein cellulose which has not been dissolved and/or suspended in step a) to a particle size below 200 nm is recycled to step a).

17. The process according to claim 1, wherein step c) comprises enzymatic hydrolysis of the cellulose.

18. The process according to claim 1, wherein step c) comprises acid hydrolysis of the cellulose.

19. The process according to claim 1, wherein the product from the hydrolysis is used for the manufacture of ethanol.

20. The process according to claim 19, wherein the ethanol is manufactured by fermentation.

* * * * *